(12) United States Patent
Hofeldt

(10) Patent No.: US 11,007,109 B1
(45) Date of Patent: May 18, 2021

(54) BINOCULAR AMBLYOPIC THERAPY

(71) Applicant: Albert Hofeldt, Miami Beach, FL (US)

(72) Inventor: Albert Hofeldt, Miami Beach, FL (US)

( * ) Notice: Subject to any disclaimer, the term of this patent is extended or adjusted under 35 U.S.C. 154(b) by 123 days.

(21) Appl. No.: 16/376,043

(22) Filed: Apr. 5, 2019

Related U.S. Application Data

(60) Provisional application No. 62/654,677, filed on Apr. 9, 2018.

(51) Int. Cl.
| | |
|---|---|
| *G02B 3/08* | (2006.01) |
| *A61H 5/00* | (2006.01) |
| *A61B 3/08* | (2006.01) |
| *A61B 3/00* | (2006.01) |
| *A61B 3/032* | (2006.01) |

(52) U.S. Cl.
CPC .......... *A61H 5/005* (2013.01); *A61B 3/0041* (2013.01); *A61B 3/08* (2013.01); *A61B 3/032* (2013.01); *A61H 2201/5007* (2013.01)

(58) Field of Classification Search
CPC .. A61B 3/08; A61B 3/04; A61B 3/032; A61B 3/022; A61B 3/0041; A61B 3/103; A61B 3/0285; A61B 3/1225; A61B 3/1015; A61H 5/015; A61H 2201/5007

USPC ....... 351/201, 200, 203, 204, 215, 222, 233, 351/234, 240, 243, 246
See application file for complete search history.

(56) References Cited

U.S. PATENT DOCUMENTS

| | | | |
|---|---|---|---|
| 8,820,930 B2 * | 9/2014 | Fateh | A61B 3/032 351/205 |
| 2013/0100400 A1 * | 4/2013 | Hofeldt | A61B 3/022 351/201 |

* cited by examiner

*Primary Examiner* — Jie Lei

(57) ABSTRACT

Active amblyopia therapy is described in this invention where the child actively participates in treatment by viewing binocular stereo image pairs in a game like experience. A method for easily measuring the amblyopic defect prior to each therapy session to validate the progress of therapy is disclosed. Therapy is provided in two embodiments viewable on graphic display devices. My first embodiment controls dominance by switching suppression between the eyes with adjustments in the rivalrous brightness balance. My second embodiment stimulates binocular pathways in both eyes using primeval motion in depth pathways where time delay between stereo images in motion produce insuppressible three dimensional effects.

3 Claims, 15 Drawing Sheets

Prior Art

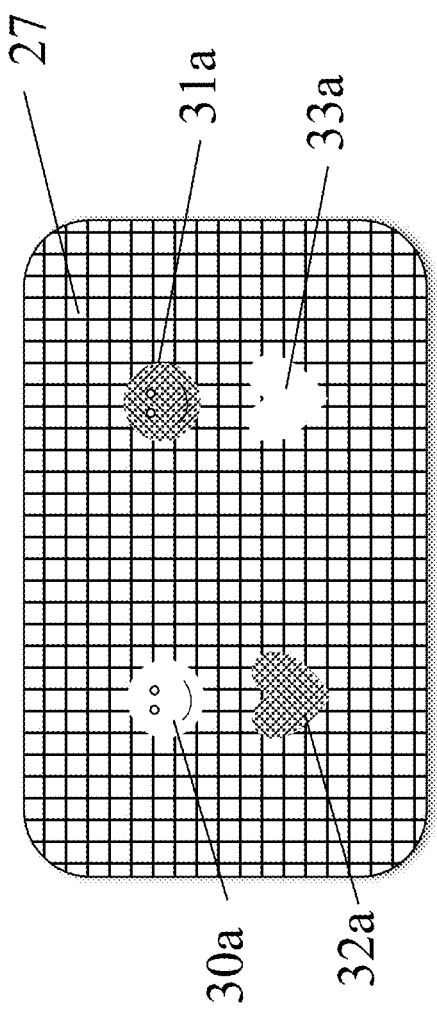
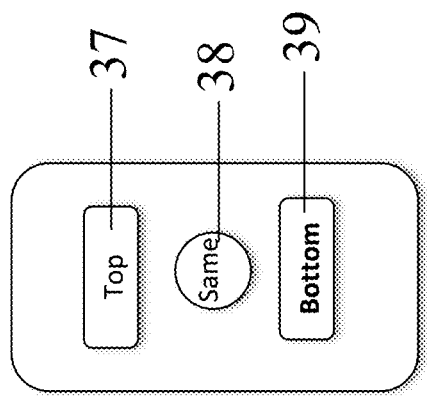
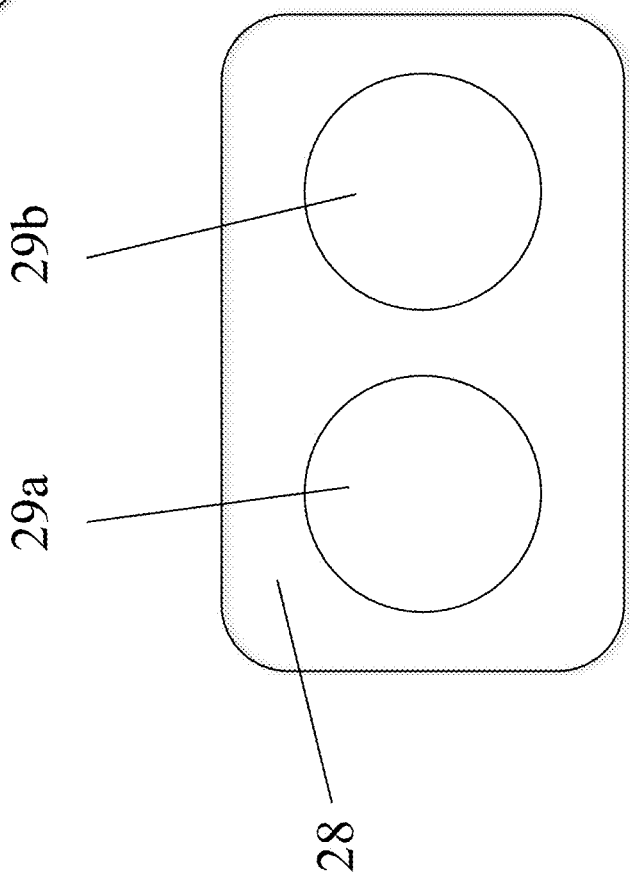
Fig. 4
Fig. 5b
Fig. 5a

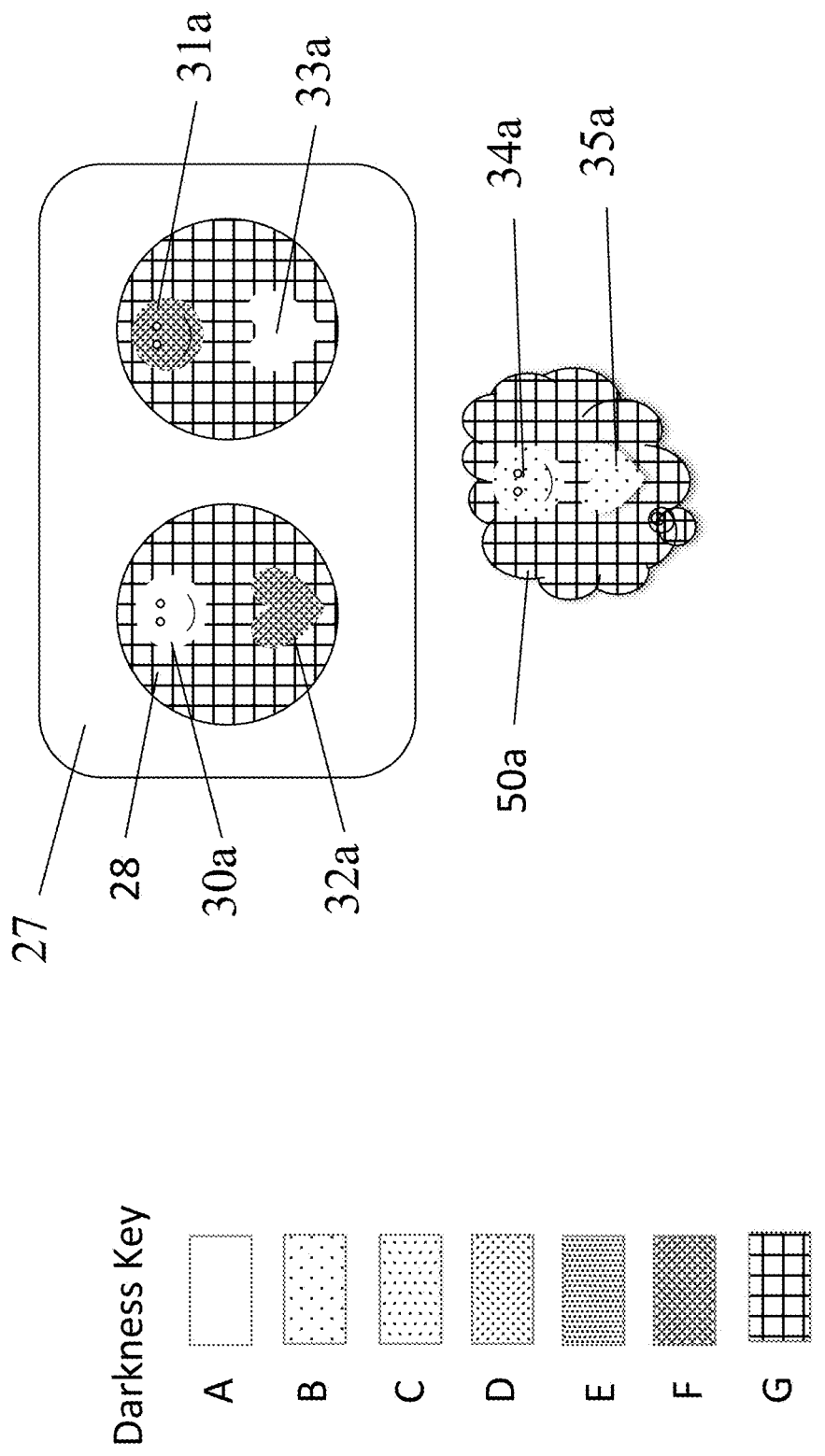

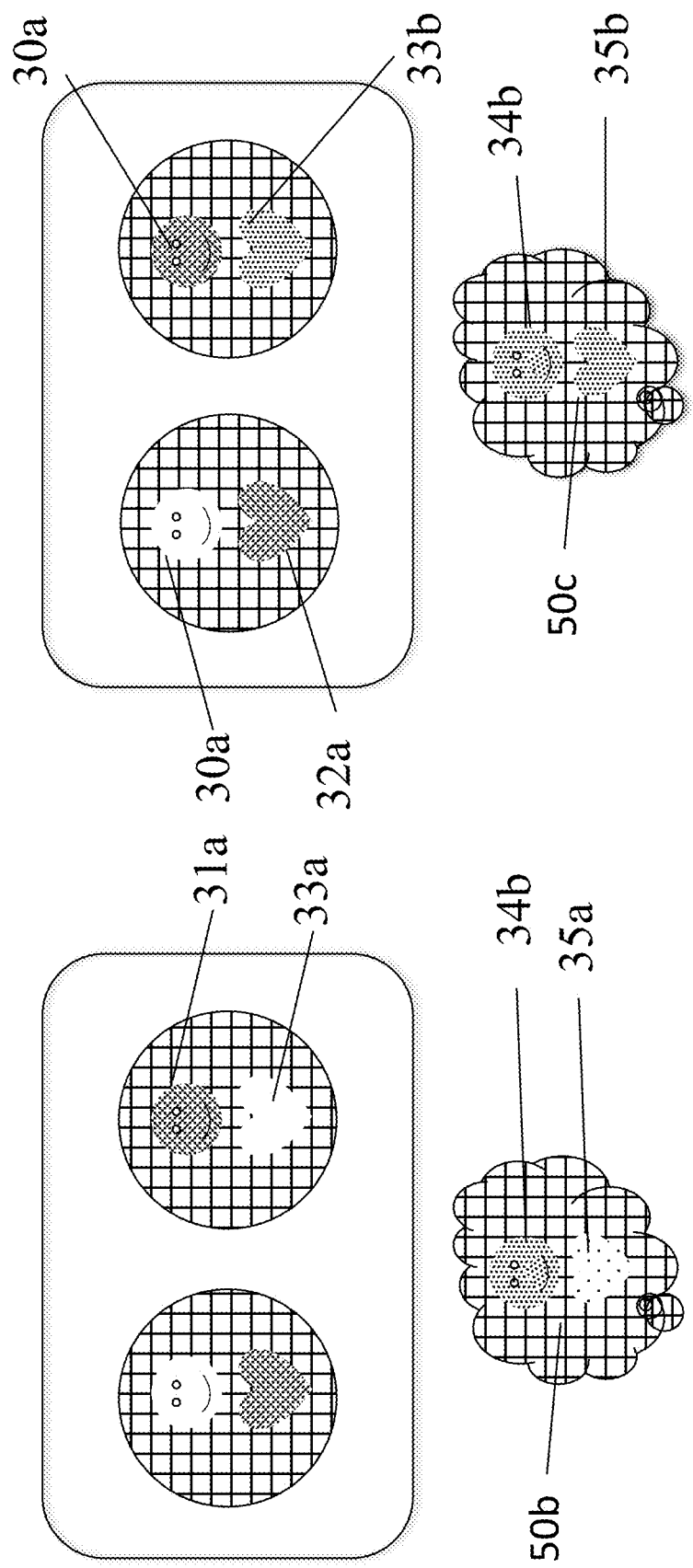

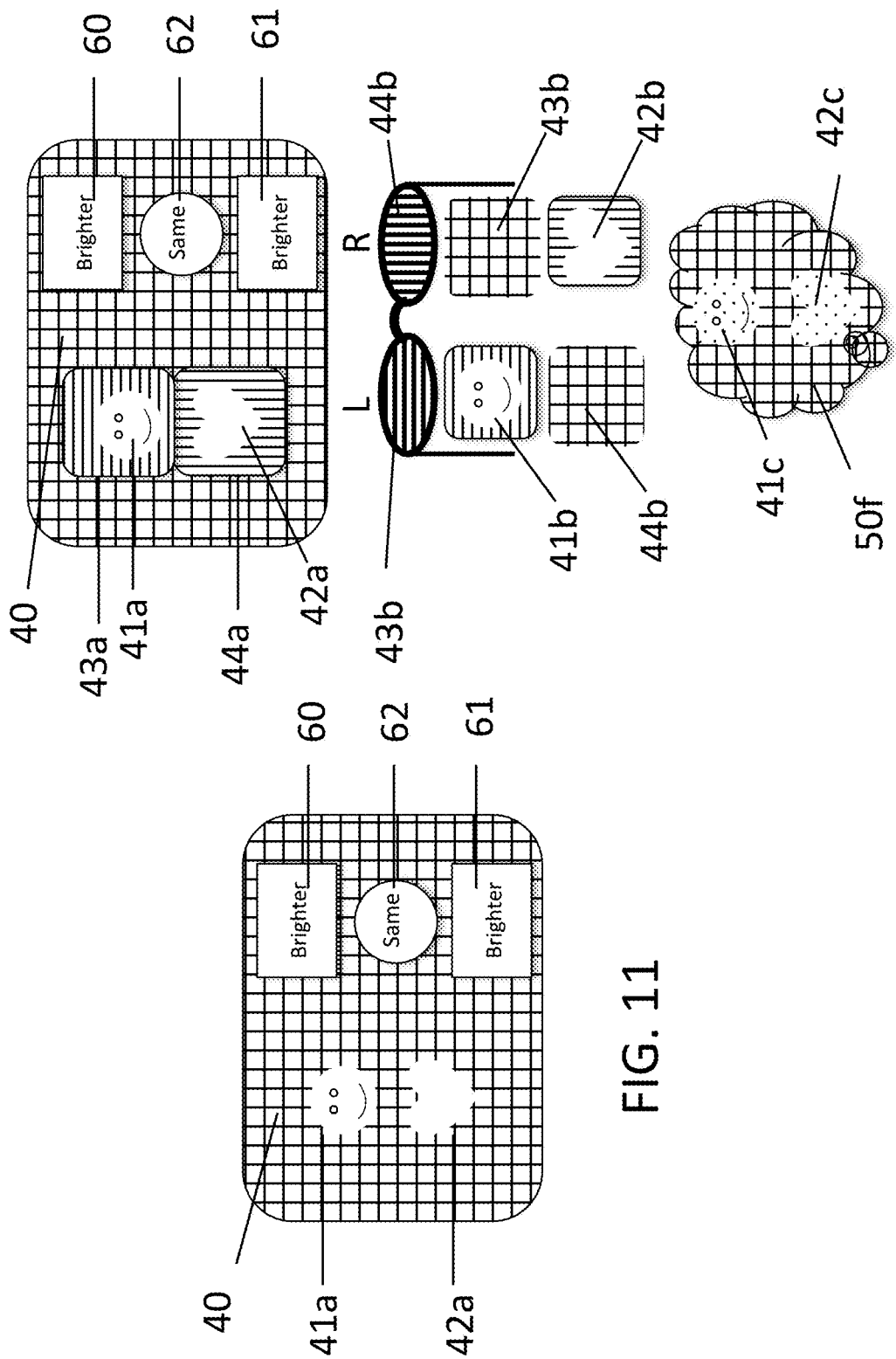

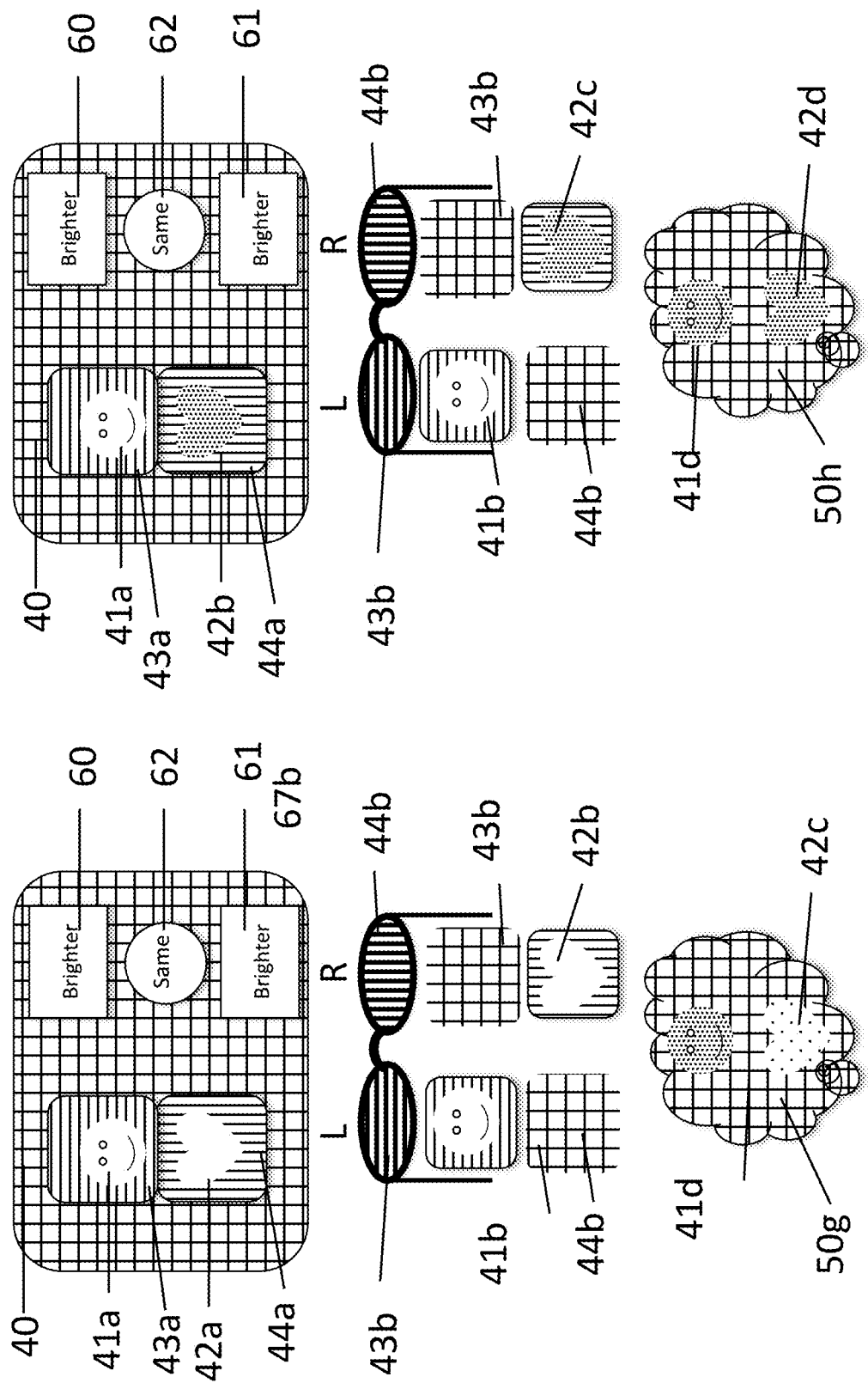

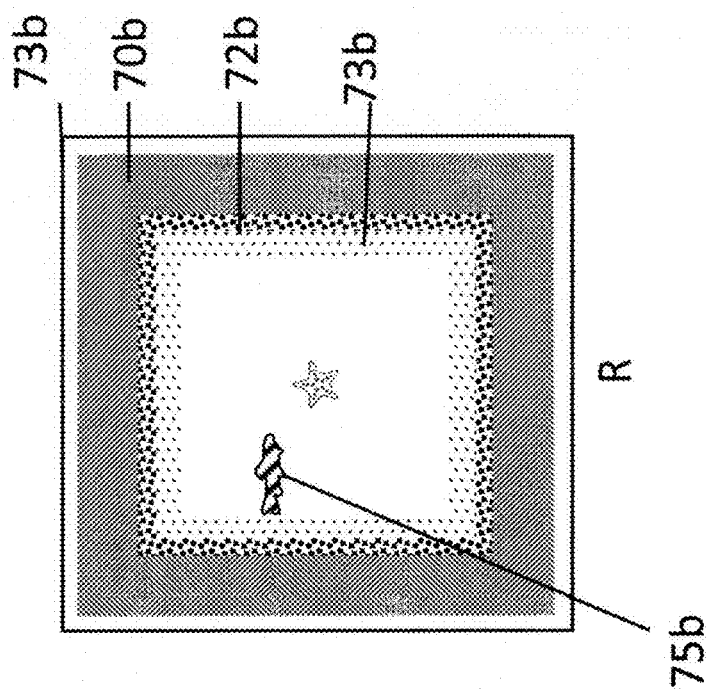
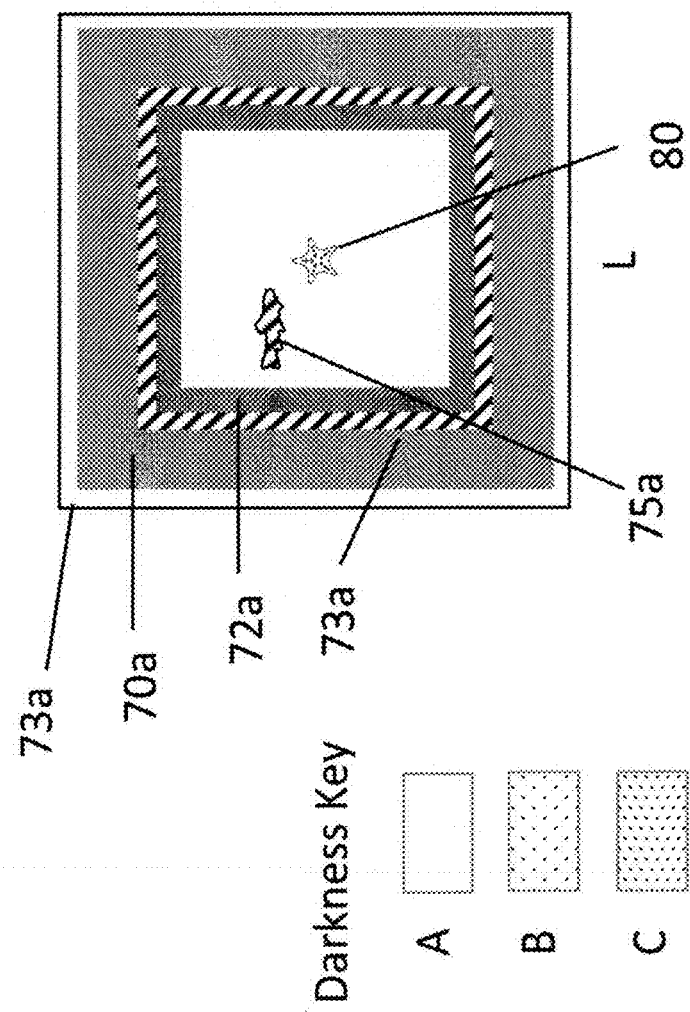
FIG. 21

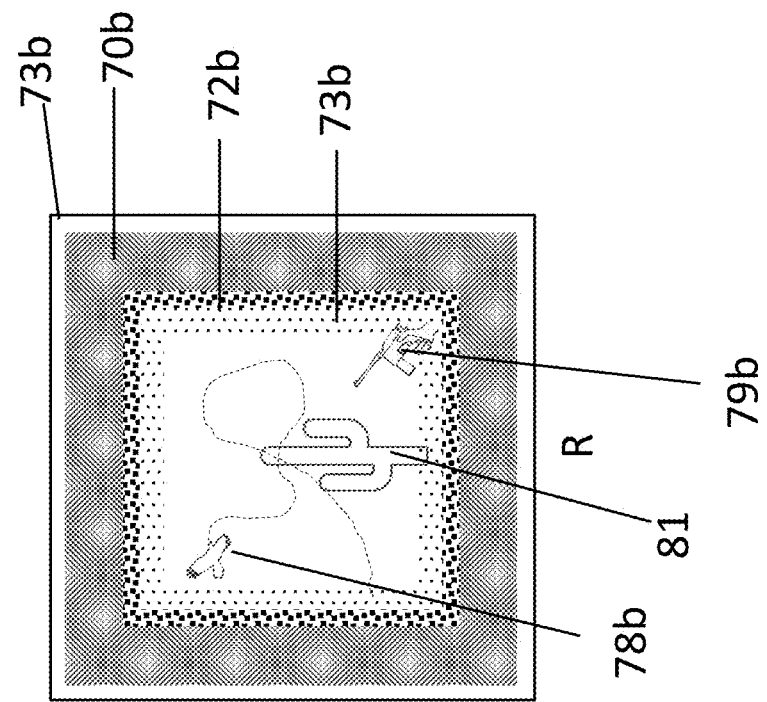
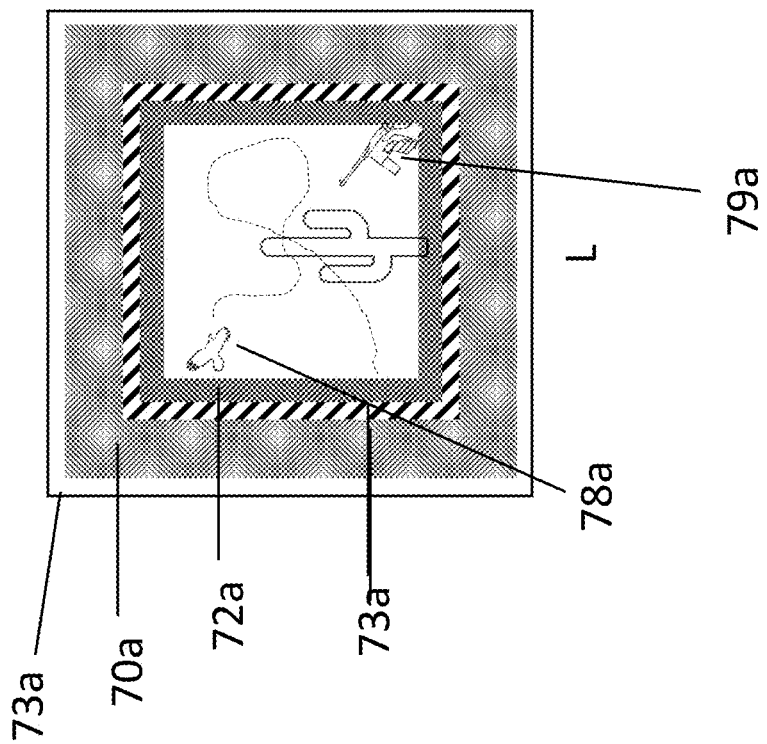
FIG. 23

BINOCULAR AMBLYOPIC THERAPY

CROSS REFERENCE TO RELATED APPLICATIONS

Provisional patent application 62/654,677 dated Apr. 9, 2018

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATED-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Field of the Invention

This invention relates to vision therapy. To be more specific, this invention pertains to binocular stimulation for treatment of amblyopia.

Related Art

U.S. Pat. No. 5,764,340, Patent Date Jun. 9, 1998. PORTABLE DEVICE FOR EVALUATING BINOCULAR VISION PROBLEMS.

U.S. Pat. No. 9,560,960, Patent Date Feb. 7, 2017. AMBLYOMETER FOR BALANCING BRIDGE RIVALROUS BINOCULAR VISION.

INTRODUCTION

Treatment of amblyopia (Lazy Eye) is commonly achieved through occlusion of the better eye and is termed passive therapy. By occluding the better eye, the patient is forced to use the lazy or amblyopic eye. Active therapies for the amblyopic defect are methods that require some activity on the part of the patient. Active methods, which may be more pleasant than passive, "penal" techniques, are intended to improve treatment of amblyopia by increased compliance during the treatment periods and the use of stimuli that may increase connectivity between certain neural pathways. For a review on the topic, I refer you to the excellent review by Catherine M Suttle BSc PhD, Clinical and Experimental Optometry, Volume 93, Issue 5, September 2010 Pages 287-299.

A powerful binocular stereoscopic stimulus is the Pulfrich phenomenon, which is an oscillating target that assumes an illusionary elliptical orbit when induced by interocular brightness disparity. The Pulfrich phenomenon is typically induced by placing a neutral density filter over one eye while observing a pendulum swinging in the frontal plane. Patients with diseases that cause an interocular brightness disparity, such as amblyopia or optic neuritis, observe the phenomenon without the need of a dimming filter, the so-called spontaneous response. Hofeldt et al. (Baseball Hitting, Binocular Vision, and the Pulfrich Phenomenon, Archives of Ophthalmology, 1996, vol. 114) reported that dimming the light to one eye with a neutral density filter of baseball hitters significantly reduced their ability to hit moving baseballs. This implies that to accurately locate a moving object the brightness balance between the two eyes is critical. Why is motion stereopsis so attuned to brightness balance? The answer is not known, but it seems reasonable to postulate that during the evolution of the visual system, natural selection for surviving moving projectiles favored accurate motion stereopsis and that visual system turned out to be based upon relative brightness. Applying this deeply rooted primeval system to improve the amblyopic defect is one innovation of my invention.

Hofeldt patent (U.S. Pat. No. 9,560,960 B2) defines the Hofeldt Bridge® which is the technique used in the DiagnosticGame® app for diagnosing amblyopia. The Hofeldt Bridge® uses vision rivalry to identify diseases, including amblyopia, that cause loss of brightness in the affected eye due to neuronal dysfunction. Vision rivalry is the simultaneous perception of dissimilar images by the two eyes. Rivalry comes in several forms, the stimuli to opposite eyes may differ in form, color and brightness, but whatever the type the competing stimuli must be similar enough for the brain to fuse the two dissimilar images into a single impression or double vision will occur. The Hofeldt Bridge® consists of at least two rivalrous stimulus pairs aligned vertically where each pair has a bright and a dim stimulus and where the bright stimulus in one pair is viewed by the left eye and in the other pair by the right eye, a reciprocal arrangement. By convention in this application, the left eye views the top impression (the top stimulus is brighter in the left eye than in the right eye) and the right eye views the bottom impression (the bottom stimulus is brighter in the right eye than in the left eye). For normal sighted people viewing two fused vertically aligned reciprocal brightness pairs of identical brightness values, the resulting top and bottom impressions appear of equal brightness. For people with defective vision in one eye causing suppression and loss of brightness, the two vertically aligned top and bottom impressions will not appear equally bright; the impression seen by the defective eye will appear dim.

In this application the Hofeldt Bridge® measures the depth of the amblyopic defect prior to starting treatment and during treatment to access the success of the treatment. The other method of assessing success of treatment is the measurement of visual acuity, the accuracy of which depends upon the preciseness of the prescription of the glasses and the cooperation of the patient. Studies have shown a direct correlation between the visual acuity and the Hofeldt Bridge® score in amblyopia. The Hofeldt Bridge® is a direct way of measuring the amblyopic defect before every therapy session and requires fewer skills of the testing personnel than vision testing. Also the Hofeldt Bridge® is incorporated into my amblyopia therapy embodiments for identifying when suppression turns into reverse-suppression as signaled by color changes of color rivalry.

In FIGS. 1 and 2 is prior art from Hofeldt patent (U.S. Pat. No. 9,560,960 B2). Illustrated in FIGS. 1 and 2 are the left and right sides of the visual system and the pathways that process images. In FIG. 1 image 1 consists of top white star 5 on a black background viewed through polarizing filter 2 and bottom white heart 4a on a black background viewed through polarizing filter 3. Heart 4a is transmitted through polarizing filters 3 and to reach the right eye while polarizing filter 6a blocks star 5 from view of the right eye. Star 5 is transmitted through polarizing filter 6b to reach the left eye while heart 4a is blocked from view of the left eye by polarizing filter 6b. The left retinal image consists of top black background 8 and bottom image star 5 and the right retinal images consist of heart 4a and black background 9. Retinal images are transmitted to optic cortex 12 via pathways 10a, 10b, 11 a and 11b where the perceived images are two rivalrous pairs, star 5 from the left eye is paired with black background 9 from the right eye and heart 4a right eye is paired with black background 8 from the left eye. The two pairs fuse to form rivalrous right dominant perception 17 and left dominant perception 18. In the absence of visual system imbalance, perceptions 17 and 18 appear equally bright since they represent the average brightness of two diametrically opposed fused image pairs of the same brightness, that is, the brighter image of each pair is stimulating opposite eyes. When the right eye sees the brighter image, the right side dominates the rivalry and when the left eye the left eye sees the brighter image, the left side dominates rivalry. The background of one image pair needs not be formless or black to achieve rivalry as illustrated in FIG. 2. By rotating polarizing filter 6b slightly away from the vertical alignment and rotating polarizing filter 6a the same amount from the horizontal alignment cross-polarization is reduced and light grey star 21 appears on background 9 and light grey heart 22 appears on background 8. At visual cortex 12, grey heart 22 and white heart 24 fuse to form right eye dominant perception 25 and white star 23 and grey star 21 fuse to form left eye dominant perceptions 26. Fused perceptions 25 and 26 appear equally bright since components, stars 21 and 23 and hearts 22 and 24, have the same average brightness.

In FIGS. 3a and 3b is prior art Hofeldt (U.S. Pat. No. 5,764,340) that teaches that rivalrous fusion of colors can detect suppression and identify the side of the amblyopic defect. In that patent, dot 100a is blue and 100b is red and when 100a and 100b fuse in the absence of a brightness defect the dot appears bluish-red in color. When the eye viewing blue dot 100a has a defect, the brain will perceive the fusion of 100a and 100b as red, the color of the dominant side, red (100b). Vice versa, when the eye viewing red 100b is the defective eye, fusion of 100a and 100b is perceived as blue (100a), the color viewed by the dominant eye. In the later Hofeldt patent (US 20130100400 A1), the rival pairs of 100a and 100b of FIG. 3a and rival pair 100b and 100a of FIG. 3b have been incorporated into a single stimulus and has become the basis of Hofeldt Bridge®. In this application color rivalry is applied in active therapy to identify the eye with the amblyopic defect and to signal when attenuation of light to the good eye is sufficient to shift the "dominance" to the amblyopic eye.

DETAILED DESCRIPTION OF THE INVENTION

This application discloses (a) means to localize and quantify the amblyopic defect and to quickly access the progress of therapy, (b) a device to administer active therapy by switching suppression between the eyes with adjustments in the rivalrous brightness balance that changes the dominance of the binocular pathways to the amblyopic eye, and (c) a device to stimulate binocular pathways in both eyes using primeval motion in depth pathways where time delay between stereo images in motion produce insuppressible three dimensional effects.

My first method for measuring the amblyopic defect is illustrated in FIG. 4, the Hofeldt Bridge® consists of at least two rivalrous stimulus pairs aligned vertically where each pair has a bright and a dim stimulus and where the bright stimulus in one pair is viewed by the left eye and in the other pair by the right eye, a reciprocal arrangement. As illustrated in FIG. 4, digital display device screen 27 is black (brightness G). The minimum requirement of the digital display device are (1) user interface for data input, (2) facility to store and archive data, (3) embedded graphics presentation program, (4) hyperlink ability, (5) Bluetooth capacity, and (6) touch screen for navigation through menus. Top rivalrous stimulus pair 30a (brightness A) and 31a (brightness F) are reciprocal in brightness to bottom rivalrous stimulus pair 31a (brightness F) and 33a (brightness A). In FIG. 5a is illustrated stereo viewer 28 having magnifying optical lenses 29a and 29b that attaches to digital display screen 27 for patient viewing. In FIG. 5b is Bluetooth remote that communicates with the program of digital display device 27, which provides for the patient to choose the brighter impression by pressing top button 37 or bottom button 39, or same brightness by pressing center button 38 (see FIGS. 5a-9). As shown in FIG. 6, normal sighted people viewing two vertically aligned reciprocal brightness pairs (pair 30a and 31a, and pair 32a and 32b) of reciprocal brightness values, the resulting top impression 34a (brightness B) and bottom impression 35a (brightness B) appear of equal brightness in mental perception 50a. For people with defective vision in one eye causing suppression and loss of brightness, the two vertically aligned top and bottom impressions will not appear equally bright. This is seen in FIG. 7, mental perception 50b of a patient with a left eye defect shows top impression 34b (brightness E) is darker than bottom impression 35a (brightness B). To measure the size of the defect in vision (suppression) in this embodiment, the brighter stimulus seen by the normal eye is darkened until the top and bottom impressions appear equally bright, which is the endpoint when the two eyes are in brightness balance. Correcting a defect in the left eye is shown in FIG. 8 by darkening stimulus 33a (brightness A) of FIG. 7 to the darkness of stimulus 33b (darkness E) achieves the endpoint where top impression 34b (brightness E) and bottom impression 35b (brightness E) appear equally bright in mental perception 50c.

A right eye defect is represented in FIG. 9 where 35c (brightness F) is darker than 34a (brightness B). Correcting this defect in the right eye is shown in FIG. 10 when darkening stimulus 30a (brightness A) of FIG. 9 to the darkness of stimulus 30b (brightness F) achieves the endpoint in FIG. 10 where top impression 34c (brightness F) and bottom impression 35c (brightness F) appear equally bright in mental perception 50e. In this example, the left eye is suppressed to equal the defective right eye. Carrying the suppression one step further leads to reverse-suppression where additional dimming of the normal eye stimulus shifts the fusion predominance to the defective eye, the defective eye becomes the dominant eye. This shift in dominance stimulates the amblyopic eye and is the basis for the first embodiment of my active amblyopic therapy.

My second method for measuring the amblyopic defect uses a double polarizing lens system as described by Hofeldt in patent (US 20130100400 A1). In this method a set of polarizing filters are placed onto the screen of a digital display device to establish the polarity of polarization. In that application, filters of similar polarity transmit light and filters of complimentary polarity block light transmission. The patient views through a second set of polarizing lenses (filters) in spectacles or other lens holding device where the polarity of the polarizing lenses has the same polarity as one of the polarizing screen filters (matched) and complementary to the filter polarity of the opposite eye. This system provides for monocular viewing of stimuli while both eyes are open. To better understand this system turn to FIGS. 11-14. In FIG. 11 is digital display device without polarizing screen filters displaying stimulus 41a (brightness A) and 42a (brightness A) of equal brightness, which are vertically aligned. In FIG. 12 polarizing screen filters 43a oriented horizontally is positioned over stimulus 41a and polarizing screen filter 44a oriented vertically is positioned over stimuli 42a. In conjunction with polarizing spectacles having left lens 43b of horizontal polarizing polarity and right lens 44b of vertical polarizing polarity monocular image separation is achieved. Top polarizing filter 43a and left polarizing lens 43b allows transmission of stimulus 41a (brightness A) to yield 41b (brightness A) and left polarizing lens 43b blocks stimulus 42a (brightness A) to yield black stimulus 44b (brightness G). Likewise, bottom polarizing filter 44a and right polarizing lens 44b allows passage of stimulus 42a (brightness A) to yield stimulus 42b (brightness A) and right polarizing lens 44b blocks stimulus 41a (brightness A) to yield black stimulus 43b (brightness G). In mental perception 50f of a normal sighted patient, top impression 41c (brightness B) the result of fusion of 41b (brightness A) and 43b (brightness G) stimuli and bottom impression 42c (brightness B) the result of fusion of 44b (brightness G) and 42b (brightness A) stimuli appear of equal brightness. The Hofeldt Bridge® is fulfilled by two pairs of rival stimuli; stimulus 41b (brightness A) verses stimulus 43b (brightness G) and stimulus 44b (brightness G) verses stimulus 42b (brightness A).

FIG. 13 illustrates a left eye defect and FIG. 14 illustrates the balancing of that left eye defect by changing the brightness of one stimulus. A defect is signaled in the left eye by the imbalance in the brightness impressions of mental perception 50g where top impression 41d (darkness E) of the left eye appears darker than bottom impression 42c (darkness B) of the right eye. The method of balancing brightness is illustrated in FIG. 14 where darkening stimulus 42a (brightness A) of FIG. 13 to stimulus 42b (brightness E) achieves the equality endpoint where top impressions 41d (brightness E) equals bottom impression 42d (brightness E) of mental perception 50h. The degree stimulus 42a is darkened is determined while the patient toggles through a series of progressive stimulus densities until discovering the endpoint, the point where top impression 41d and bottom impression 42d in mental perception 50h appears equally bright. The left eye is suppressed to equal the suppression caused by the right eye defect. Continuing to dim the normal eye will lead to reverse-suppression where the defective eye becomes dominant and the fusion process in the defective eye predominates, which is the foundation for Hofeldt Bridge® amblyopia therapy.

FIG. 15 illustrate a right defect and FIG. 16 illustrates the balancing of that right eye defect by changing the brightness of one stimulus. A defect is signaled in the right eye by the imbalance of brightness impressions in mental perception 50i where bottom impression 42c (darkness E) of the right eye appears darker than top impression 41c (darkness B) of the left eye. The method of balancing brightness is illustrated in FIG. 16 where darkening stimulus 41a (brightness A) of FIG. 15 to stimulus 41b (brightness E) achieves the equality endpoint where top impressions 41c (brightness E) equals bottom impression 42c (brightness E) of mental perception 50j. The degree stimulus 41a is darkened is determined when the patient toggles through a series of progressive stimulus densities until the endpoint is reached, the point where top impression 41c and bottom impression 42c in mental perception 50j appears equally bright.

In FIG. 17 is illustrated reverse-suppression of the right defect illustrated in FIG. 16 where top stimulus 41d (darkness F) is darker than bottom impression 42c (darkness E) of mental perception 50k. In this example the left normal eye is more suppressed than the defective right eye and the right eye becomes dominant. One method for the patient to indicate their selection of brightness is hyperlink buttons 60 and 61 illustrated in FIG. 18. When the top impression is brighter, button 60 is activated, when the bottom impression is brighter, button 61 is activated and when equal, button 62 is activated.

In FIG. 19 is illustrated a table that stores the patient's response to each brightness choice in a series of stimuli presentations. The presentation program may be an app or a presentation program such as PowerPoint where links are programed to record correct and incorrect responses and the time elapse of active therapy segments, parameters adjustable in setting of the graphic display device. In FIG. 19, "Top" choice for Slides 1-3 shows the left eye is dominant (chosen as brighter), the "Same" choice for Slide 5 and 9 indicates equal balance of the right and left eyes, Slides 5-8 show the right eye is dominant and Slide 10 shows the dominance has switched back to the left eye.

My first therapeutic embodiment dims one image of an image pair to use brightness rivalry to switch the dominance from the normal eye to the amblyopic eye which is similar to dimming one image of a image pair in the Hofeldt Bridge®. In FIG. 20 is an example of image arrangement for viewing stereo image pairs in the form of still or movie stereo images where 75a and 75b are stereo pairs. Sheets 73a and 73b overlay images 75a and 75b as front digital sheets capable of attenuating light and thereby able to dim images 75a or 75b. Dimming the right or left side to suppress the non-amblyopic eye during therapy can be achieve by (1) a series of sheets 73a or 73b of increasing opacity (darker) where the brightness of one eye is sequentially reduced or (2) by progressively dimming a single image using the variable opacity feature within the presentation by program algorithms.

Two fusible complementary colors serve to signal suppression/dominance rivalrous status: red line 72a and blue line 72b. When the left eye is dominant, the patient sees red line 72a and when the right eye is dominant the patient sees blue line 72b. Frame 70a and 70b are the identical color, which makes a strong stimulus for binocular fusion. The perceived color of fusion of lines 72a and 72b identifies the dominant eye, when blue is perceived by the non amblyopic eye and red is perceived by the amblyopic eye at reverse-suppression the perceived color will change from blue to red. Lines 73a and 73b of rival shades of gray add contrast and makes the perceptual difference of right or left dominance more obvious. In the absence of suppression, the patient perceives simmering bluish-red color as 72a and 72b fuse. Other fusible colors may be used.

For therapy three series of stereo images pairs are available where right images are dimmed and three series where the left images are dimmed. The series vary by the difference in brightness between the right and left images of 0.6, 1.2, and 1.8 log units. These log units represent the initial interocular brightness of therapy, as the movie plays the interocular gradually increases to 2.4 log units. Other values for interocular brightness difference could be used. The rivalrous color-coding is such that the red is on the side of the amblyopic eye so that at the point of reverse-suppression the frame turns from blue to red. Typically the duration of each movie is 2 to 5 minutes and the series may contain 10 movies or more of different animals or other subjects. My preferred subject matter is stereo movies of zoo animals because animals interest children.

The testing protocol is (1) establish the size and side of the patient's amblyopic defect with the Hofeldt Bridge®, (2) select the series of stereo movies that (a) dims the side of the non-amblyopic eye and (b) where the interocular brightness difference is the same or greater than the patient's defect (patient defect is 0.8 log choose 0.9 log movie for therapy) (3) while the patient watches the stereo movies within a stereo viewer, the program will gradually dim the light to the non-amblyopic eye and the patient is to signal when the rivalrous color frame around the images change color from blue to red which confirms viewing is in the reverse-suppression status, which gives maximum stimulation to the amblyopic eye.

My second therapeutic embodiment is seen in FIG. 21 where the motion disparity is generating the Pulfrich effect in stereo image pairs by time delay of one image of the image pair and not by brightness disparity. This technique is a side door into the Pulfrich effect that requires no interocular brightness disparity and the depth effect can be as much or more than the original effect produced brightness disparity. The delay in motion between paired images produces the perception of depth and that depth perception therapeutically stimulates the binocular stereoscopic pathways. Star 80 is a reference point for judging depth perception. Images 75a and 75b constitutes a stereo pair. When moving along a straight path from left to right, delaying left image 75a causes a posterior arching path and delaying right image 75b causes an anterior arching path. Similarly, when moving from right to left along a straight path, delaying right image 75b causes a posterior arching path and delaying left image 7a causes an anterior arching path. There can be one or multiple image pairs and the delay between the image pairs could vary as long as the delay is within the limit of fusion disparity as long as image pairs follow the identical path.

In FIG. 22 second stereo pair 76a and 76b is added, which fulfills the requirements for Hofeldt Bridge® for color rivalry, that is, two fusible rivalrous image pairs where image colors are reciprocally arranged. This is illustrated by the color-coded images: 75a and 76b are red and 75b and 76a are blue forming the reciprocal rivalrous configuration of the Hofeldt Bridge® in color. In the absence of suppression the fusion of 75a (red) and 75b (blue) forms impression 71a of red-blue color and fusion of 76a (blue) and 76b (red) forms impression 71b of red-blue color as seen in perception 50i in FIG. 22. When the left eye is suppressed, fusion of left 75a (red) and right 75b (blue) produces blue (71a) and the fusion of left 76a (blue) and right 76b (red) turns red (71b). The opposite occurs when the right eye is suppressed. Suppression and reverse suppression can be identified be the color of 71a and 71b, which signals the dominance status of the eyes. Substituting gray scale colors for red and blue in the rivalrous image pairs above, this embodiment fulfills the requirement of the Hofeldt Bridge® to measure brightness balance.

In FIG. 22 is illustrated the Pulfrich effect in a game format where bird 77a and 77b are image pairs travelling along a circuitous path within the visual space and a delay in motion between the two produces perception of depth. Cactus 81 within the visual space is a reference point for depth perception. Gun image pair 79a and 79b in an interactive link within the presentation program that when triggered sends projectiles image 80a and 80b from gun 79a and 79b along a path that collides with bird 77a and 77b. Bird 77a and 77b along with projectiles 80a and 80b provide exercise of the binocular visual pathways. Giving rewards for hits could provide an incentive for children and encourage therapy. This is one format for a game and others standard gaming techniques could be applied for those skilled in the art of programming.

For therapy three series of stereo images pairs are available where right images are dimmed and three series where the left images are dimmed. The series vary by the difference in brightness between the right and left images of 0.6, 1.2, and 1.8 log units. These log units represent the initial interocular brightness in a movie, as the movie plays the interocular gradually increases to 2.4 log units. Other values for interocular brightness difference could be used. The rivalrous color-coding is such that the red is on the side of the amblyopic eye so that at the point of reverse-suppression the frame turns from blue to red. Typically the duration of each movie (or animated presentation) is 2 to 5 minutes and the series may contain 10 movies or more of different animals or other subjects.

As with my first embodiment, two fusible complementary colors serve to signal suppression/dominance rivalrous status as seen in FIG. 22: red line 72a and blue line 72b. When the left eye is dominant, the patient sees red line 72a and when the right eye is dominant the patient sees blue line 72b. Frame 70a and 70b are the identical color, which makes a strong stimulus for binocular fusion. The perceived color of fusion of lines 72a and 72b identifies the dominant eye, when blue is perceived by the non amblyopic eye and red is perceived by the amblyopic eye at reverse-suppression the perceived color will change from blue to red. Lines 73a and 73b of rival shades of gray add contrast and makes the perceptual difference of right or left dominance more obvious. In the absence of suppression, the patient perceives bluish-red simmering color of the fusion of 72a and 72b. In addition to the color-coded frame, the stereo images may be color-coded. For example if the image pair consists of a red and a blue fish and the amblyopic eye views the red fish, upon reverse-suppression the fish changes from blue to red. Other fusible colors may be used.

The testing protocol is (1) establish the size and side of the patient's amblyopic defect with the Hofeldt Bridge®, (2) select the series of stereo movies (or other media) that (a) dims the side of the non-amblyopic eye and (b) where the interocular brightness difference is the same or greater than the patient's defect (patient defect is 0.8 log choose 0.9 log movie that dims the non amblyopic eye for therapy) (3) while the patient watches the stereo movies within a stereo viewer, the program gradually dims the light to the non-amblyopic eye and the patient is to signal when the rivalrous color frame around the images change color from red to blue which signals that viewing is in the reverse-suppression status, which gives maximum stimulation to the amblyopic eye.

For both embodiments, the stimulus variety is endless which includes but is not limited to animated stimuli, flashing lights, animals, objects, letters, numbers, symbols, colors, and graphic designs. The program should keep the patient interested and preferably entertained. Accuracy and timing rewards may be offered for encouragement.

Figure 2:
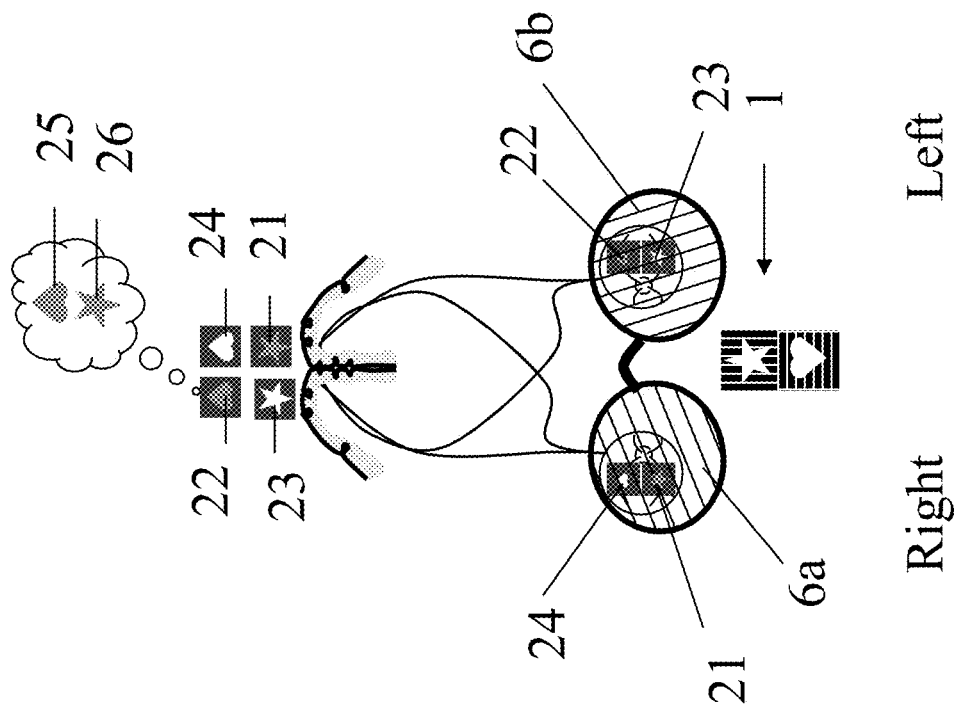
Figure 1:
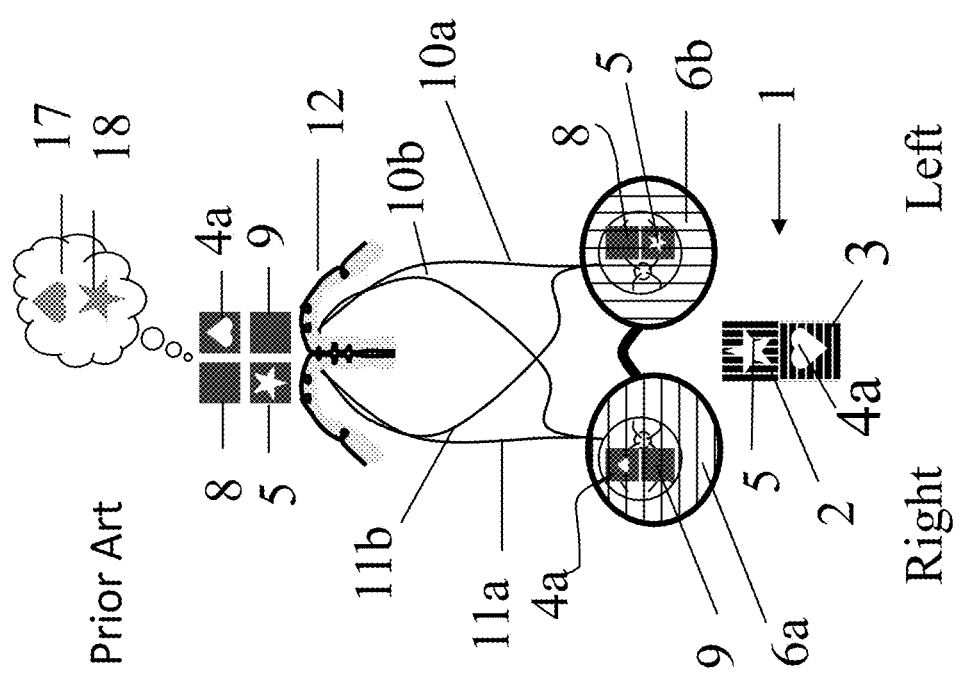
FIG. 1. Prior Art, Hofeldt Bridge®, 2017
FIG. 2. Prior Art, Hofeldt Bridge®, 2017
FIGS. 3a and 3b. Prior Art, Hofeldt, 1998
FIG. 4. Graphic display device displaying Hofeldt Bridge®
FIG. 5a. Stereo viewer
FIG. 5b. Remote control
FIG. 6. Normal, balanced brightness
FIG. 7. Left eye defect imbalanced
FIG. 8. Left eye defect balanced
FIG. 9. Right eye defect imbalanced
FIG. 10. Right eye defect balanced
FIG. 11. Graphic display device without filters displaying images and controls
FIG. 12. Double polarizing filters with polarizing glasses, balanced brightness
FIG. 13. Left eye defect, double polarizing filters
FIG. 14. Left eye defect, balanced
FIG. 15. Right eye defect, double polarizing filters
FIG. 16. Right eye defect, balanced
FIG. 17. Reverse-suppression, double polarizing filters
FIG. 18. Remote control
FIG. 19. Data collection file
FIG. 20. Embodiment 1, brightness balance and dominant switching therapy
FIG. 21. Embodiment 2, primeval motion in depth rivalry therapy
FIG. 22. Rivalrous color-coded images of Hofeldt Bridge®
FIG. 23. Game format, primeval motion in depth therapy
Figure 3A:
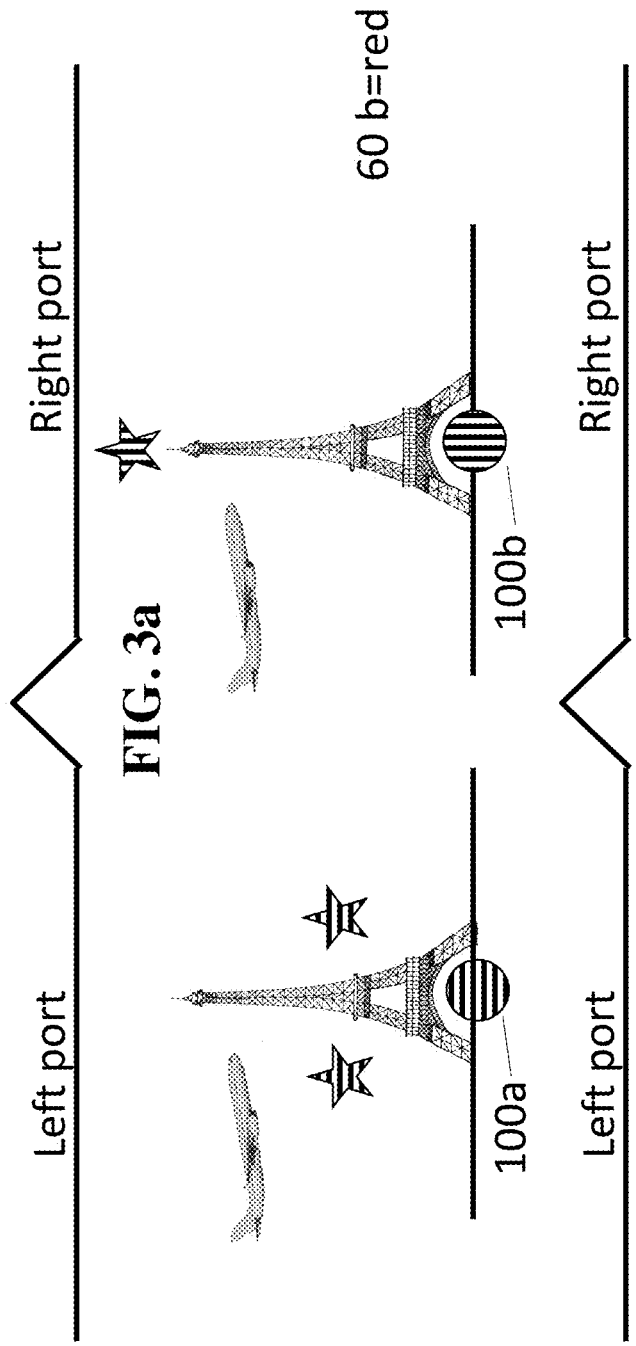
Figure 3B:
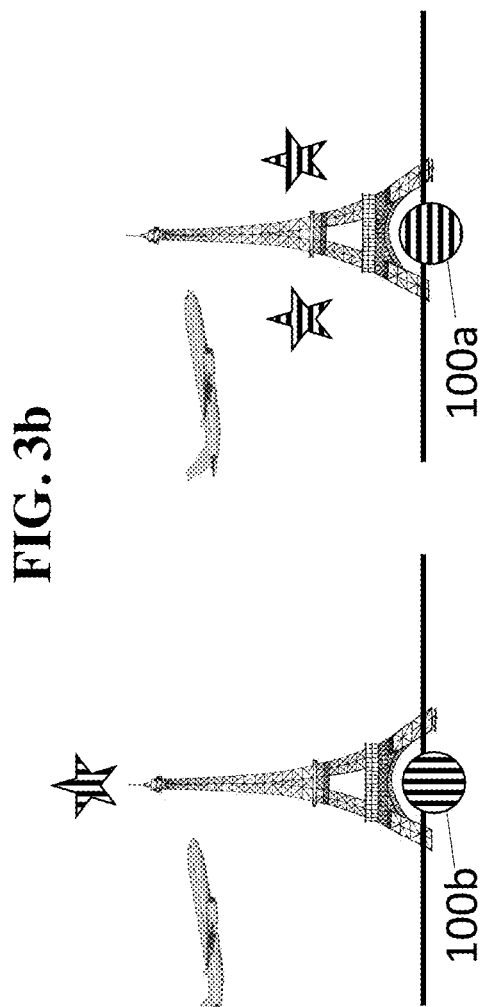
Figure 10:
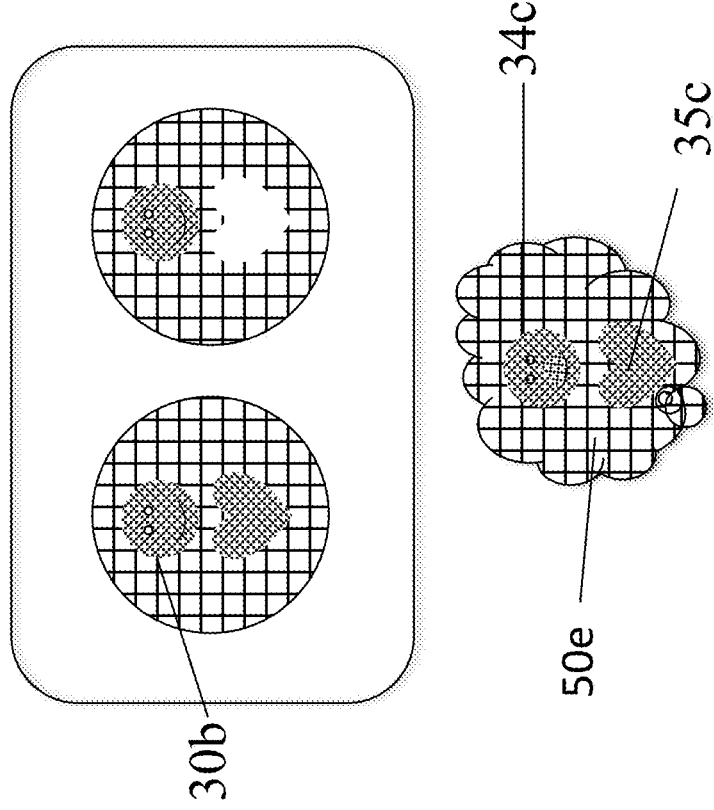
Figure 9:
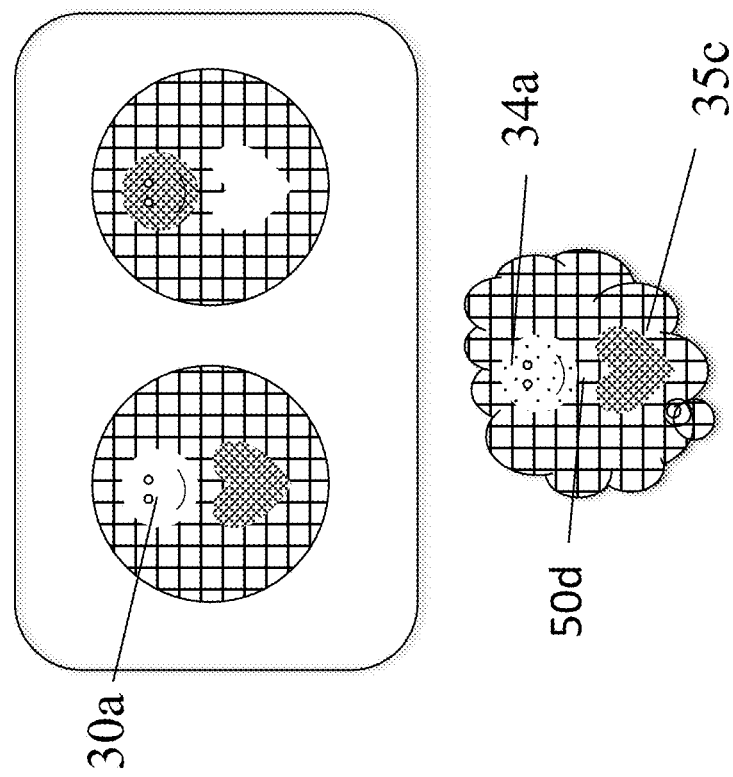
Figure 16:
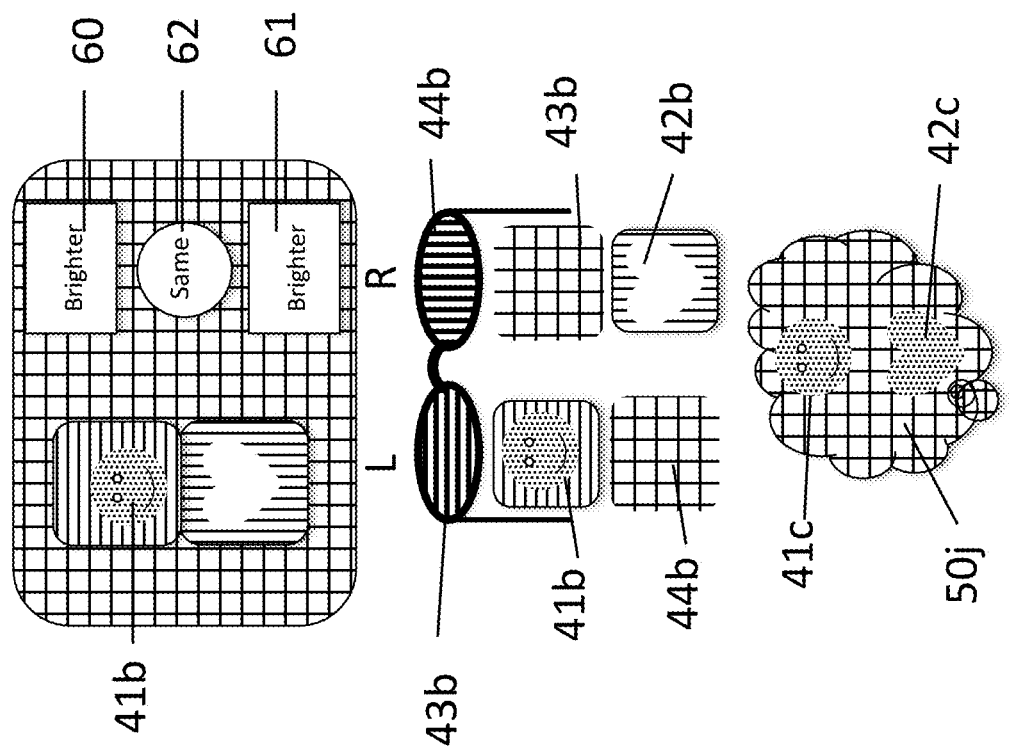
Figure 15:
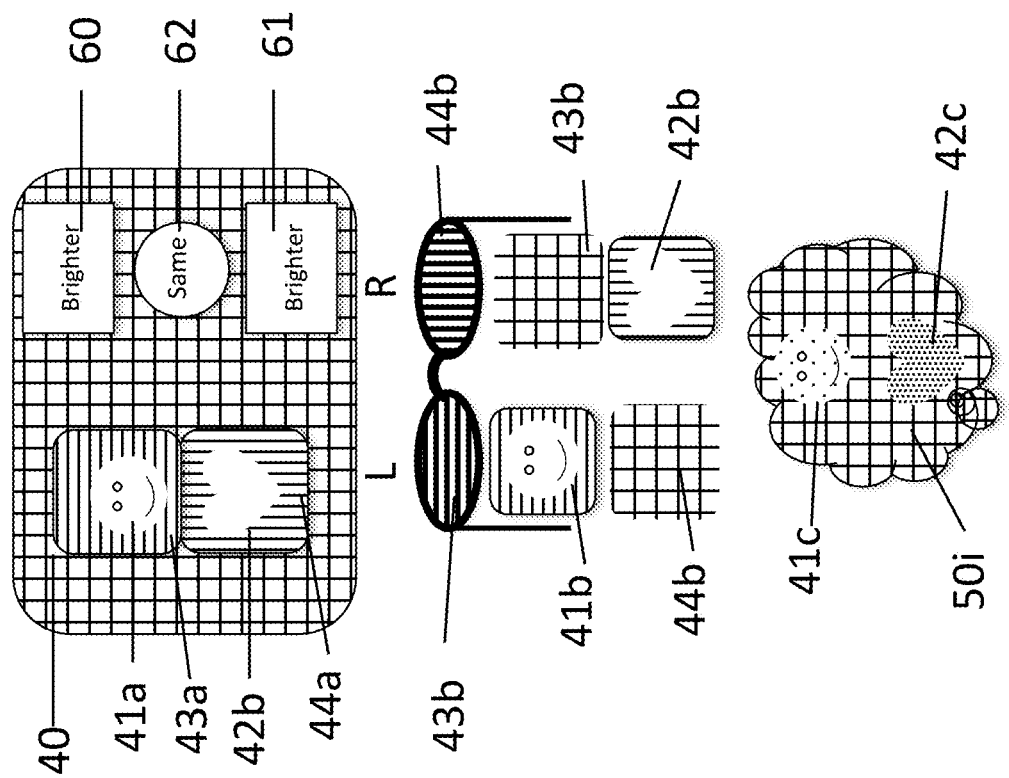
Figure 18:
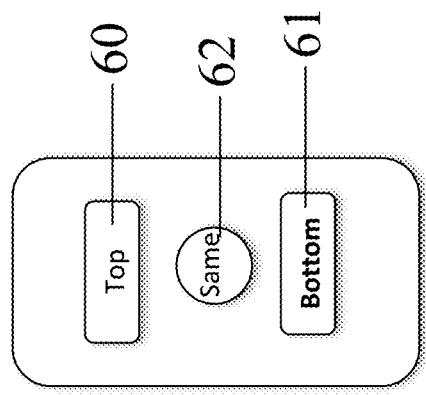
Figure 17:
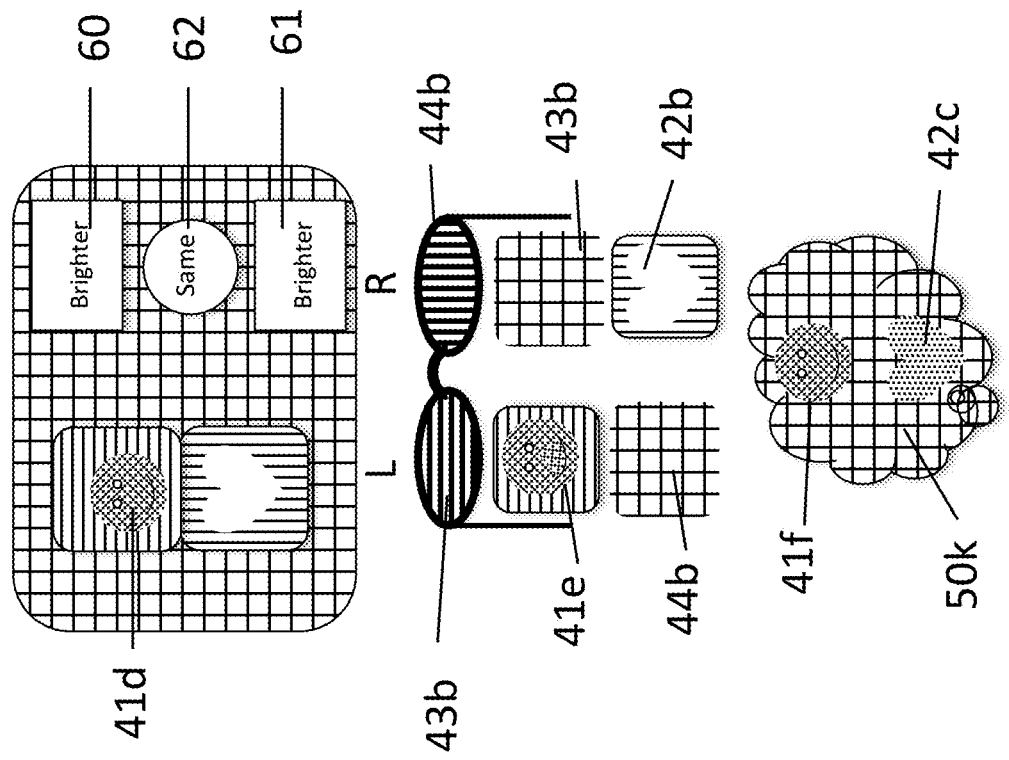
Figure 19:
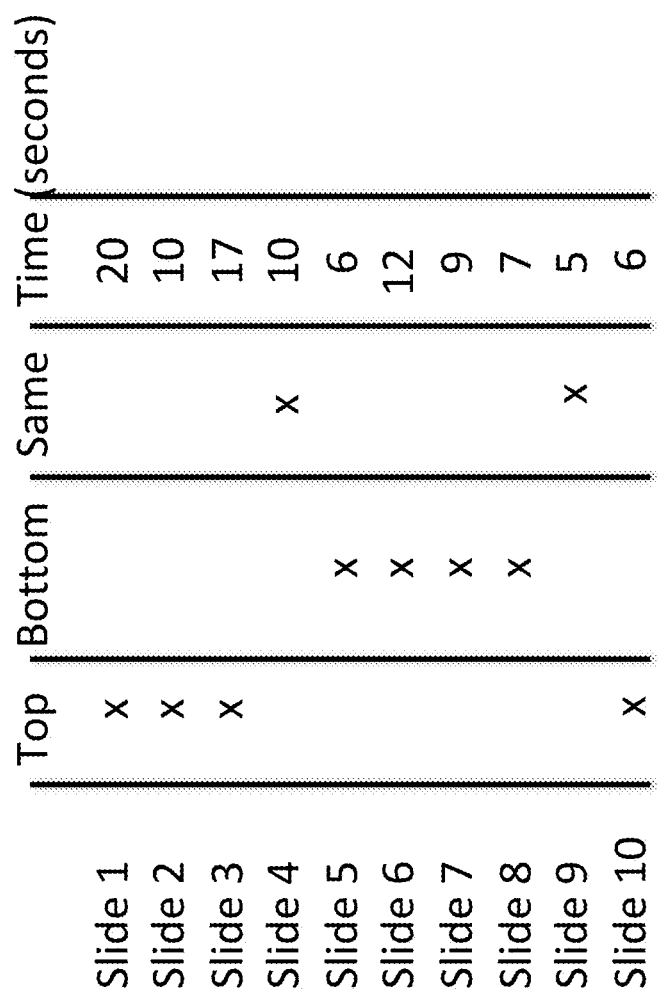
Figure 20:
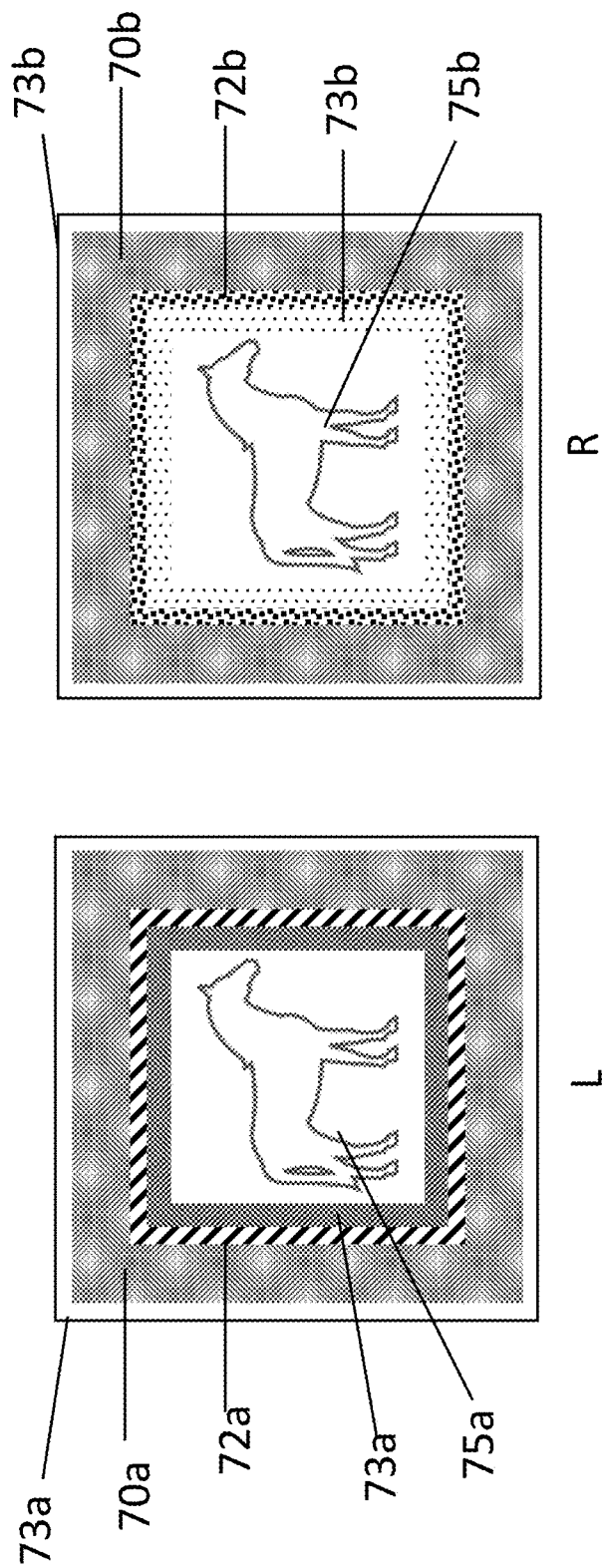
Figure 22:
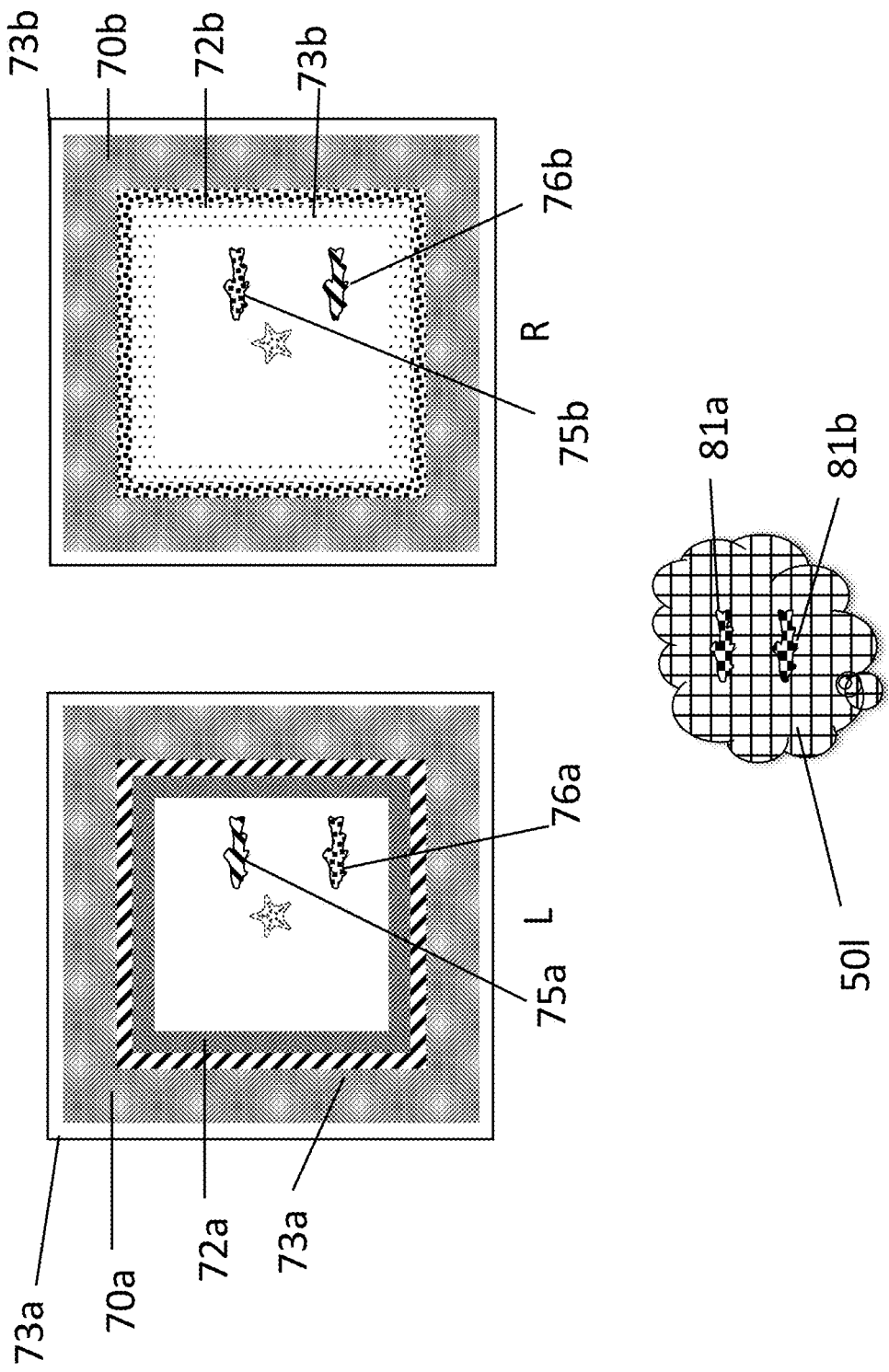

The invention claimed is:

1. A device for active amblyopic therapy by stimulation binocular visual pathways by images in motion comprising:
   a. a graphic display device having touch screen and data storage and capable of still and movie presentations and hyperlinking,
   b. stereo viewer housing said graphic display device,
   c. a stereoscopic presentation program viewable by the right and left eyes within a stereo viewer having a stereo image pair where the right image of a stereo pair is presented to the right eye and the left images of said stereo pair is presented to the left eye of a patient and where said right and left images are in motion along an identical path at the same speed but where said right and said left images are separated by a time delay producing the perception of stereoscopic depth,
   d. where the time delay can vary as long as the delay is within the limit of fusion disparity, and
   e. an identical reference image located in the center of the visual area of each eye.

2. The method of claim 1 where more than one images pairs are moving in said visual space, the movement is back and forth across said visual space and the movement can be in a straight line or circuitous.

3. The method of claim 1 where the subject can interact through hyperlinks to trigger projectiles aimed at the moving image pair.

* * * * *